(12) United States Patent
Liu et al.

(10) Patent No.: US 9,877,726 B2
(45) Date of Patent: Jan. 30, 2018

(54) OCCLUSION DEVICE AND METHOD FOR ITS MANUFACTURE

(75) Inventors: Xiangdong Liu, Shenzhen (CN); Weijun Zeng, Shenzhen (CN)

(73) Assignee: Lifetech Scientific (Shenzhen) Co., Ltd. (CN)

( * ) Notice: Subject to any disclaimer, the term of this patent is extended or adjusted under 35 U.S.C. 154(b) by 524 days.

(21) Appl. No.: 13/823,869

(22) PCT Filed: Oct. 25, 2010

(86) PCT No.: PCT/CN2010/078075
§ 371 (c)(1),
(2), (4) Date: Mar. 15, 2013

(87) PCT Pub. No.: WO2012/034298
PCT Pub. Date: Mar. 22, 2012

(65) Prior Publication Data
US 2013/0178886 A1 Jul. 11, 2013

(30) Foreign Application Priority Data
Sep. 16, 2010 (CN) .......................... 2010 1 0283652

(51) Int. Cl.
*A61B 17/12* (2006.01)
*A61B 17/00* (2006.01)
*D04C 1/06* (2006.01)

(52) U.S. Cl.
CPC .... *A61B 17/12109* (2013.01); *A61B 17/0057* (2013.01); *A61B 17/12172* (2013.01);
(Continued)

(58) Field of Classification Search
CPC .......... A61B 17/12172; A61B 17/0057; A61B 2017/00623; A61B 2017/00592;
(Continued)

(56) References Cited

U.S. PATENT DOCUMENTS 5,334,217 A * 8/1994 Das ............................... 606/213
7,004,967 B2 * 2/2006 Chouinard et al. .......... 623/1.15
(Continued)

FOREIGN PATENT DOCUMENTS

EP 2387951 11/2011
WO WO2011/147784 12/2011

*Primary Examiner* — Eric Rosen
*Assistant Examiner* — Mikail Mannan
(74) *Attorney, Agent, or Firm* — Raymond Sun

(57) ABSTRACT

An occlusion device comprises a distal end, a proximal end and an elastic braided body which is provided between the proximal end and the distal end and made of wires. The elastic braided body is composed of a multi-stage braided net, which comprises at least a first-stage braided net that is closest to the distal end and made of a plurality of first-stage wires, and a second-stage braided net which is braided by a plurality of first-stage wires and second-stage wires all together. The minimum cross-section area of the first-stage braided net after being compressed toward the direction perpendicular to an axis of the elastic braided body is less than the minimum cross-section area of any other-stage braided net after being compressed toward the axis. A method for manufacturing the occlusion device is also provided.

11 Claims, 13 Drawing Sheets

(52) U.S. Cl.
CPC ...... *D04C 1/06* (2013.01); *A61B 2017/00004* (2013.01); *A61B 2017/00526* (2013.01); *A61B 2017/00592* (2013.01); *A61B 2017/00606* (2013.01); *A61B 2017/00867* (2013.01); *D10B 2509/06* (2013.01)

(58) Field of Classification Search
CPC   A61B 2017/00654; A61B 2017/00597; A61B 2017/00575; A61B 2017/00659; A61B 2017/00867; A61B 2017/00606; A61B 2017/00004; A61B 2017/00579; A61B 2017/00632; A61B 2017/00641; A61B 17/12122; A61B 17/1214; A61B 17/12145; A61B 17/12168
USPC ...................................... 623/23.72
See application file for complete search history.

(56)  References Cited

U.S. PATENT DOCUMENTS

| | | | |
|---|---|---|---|
| 2006/0241690 A1* | 10/2006 | Amplatz et al. | 606/213 |
| 2007/0167980 A1* | 7/2007 | Figulla et al. | 606/213 |
| 2007/0265658 A1* | 11/2007 | Nelson et al. | 606/213 |
| 2008/0262518 A1* | 10/2008 | Freudenthal | A61B 17/0057 606/151 |
| 2009/0099647 A1* | 4/2009 | Glimsdale et al. | 623/1.35 |
| 2011/0152993 A1* | 6/2011 | Marchand | A61B 17/12022 623/1.2 |
| 2011/0184439 A1* | 7/2011 | Anderson | A61B 17/0057 606/151 |

\* cited by examiner

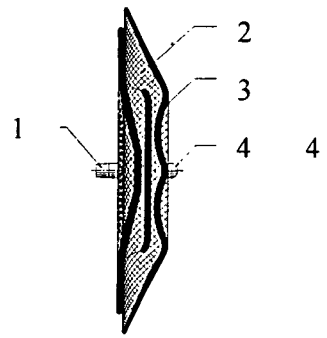
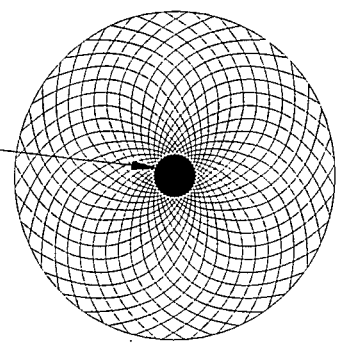
FIG.1　　　　　　　　FIG.2
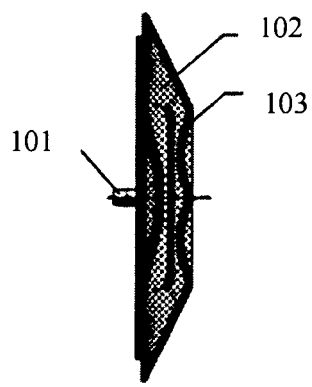
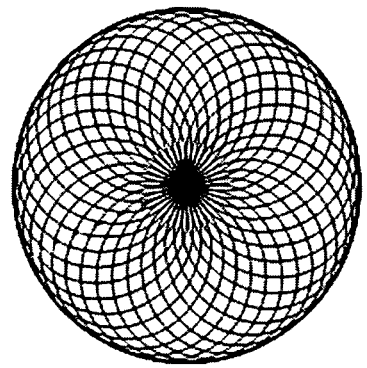
FIG.3　　　　　　　　FIG.4

OCCLUSION DEVICE AND METHOD FOR ITS MANUFACTURE

TECHNICAL FIELD

The present invention relates to a medical device and the manufacturing, method therefore. In particular, the present invention relates to an interventional treatment device for occluding defects in heart or blood vessels and the manufacturing method thereof.

BACKGROUND

In company with the continuous development of interventional materials and devices as well as interventional cardiology, minimally invasive treatment using an interventional occluder via catheter has become an important method for treating ventricular septal defect (VSD), atrial septal defect (ASD), patent ductus arteriosus (PDA), patent foramen ovale (PFO) and other congenital heart diseases. In addition, it is a widely accepted treatment method for carrying out endovascular closure using an intervention means.

For example, Chinese Patent No. 97194488.1 discloses a heart occluder. As shown in FIGS. 1 and 2, this heart occluder comprises bolt head 1, metal mesh 2, flow-occluding membrane 3, and closure head 4. As shown in FIG. 5, a steel sleeve 6 used for fixing metal mesh 2 is provided at one end of bolt head 1. Steel sleeve 6 is fitted and fixed by means of welding in blind hole 7 at one end of bolt head 1. As a result, the entire metal mesh 2 is connected to bolt head 1, forming one end of the wires 201 of the metal mesh 2 and one welding head 203. An internally threaded bore 8 is formed at the other end of bolt head 1. Said internally threaded bore 8 is used to connect and fix the device that transports the occluder.

In addition, for example, Chinese Patent No. 200780010436.7 discloses an occluder. As shown in FIGS. 3 and 4, this occluder comprises bolt head 101, metal mesh 102, and flow-occluding membrane 103. The structure of the bolt head is basically the same as that shown in FIG. 5. This structure has no closure head compared with FIG. 1, and the braided mesh has an integral closed structure.

Although the aforementioned two occluders can occlude cardiac septal defects or blood vessels, they both have obvious structural defects. The structure shown in FIG. 1 has a permanent closure head at the distal end (the distal end is defined as the end that is away from the operator during the operation). As a result, the amount of the metal left in the human body is increased. If the closure head and the metal mesh are made of different metal materials, local galvanic corrosion will occur, and the electric field thereof will damage the physiological environment of the surround tissues and increase the risk of having broken metal wires at that location. The large amount of metal ions released also has an adverse effect on the surrounding tissues over the long term. Meanwhile, since the closure head sticks out permanently, it not only causes long-term damage to the tissues inside the heart but also is not conducive to epithelialization by the endothelial tissue. The structure shown in FIG. 3 has no closure head so that the aforementioned risk can be avoided. However, when this occluder is placed back into the sheath, serious accumulation of metal wires will occur at the distal end. As a result, the resistance incurred when placing the occluder back into the sheath during the surgery becomes excessively large (if a larger sheath is used, extra damage will be caused by the sheath to the vascular wall). The risk of the surgery is increased. Meanwhile, the application range of the device is reduced.

DISCLOSURE OF THE INVENTION

Technical Problem

The objective of the present invention is to provide an occluder and the manufacturing method thereof, which can solve the problems of the prior art, that is, the long-term damage caused by the permanent closure head to the tissues inside the heart, the long-term corrosion caused by different kinds of metals at the closure head, accumulation of the wires at the distal end of the occluder that increases the resistance incurred when placing the occluder back into the sheath, and the problem that the conventional occluder is relatively difficult to adapt to a smaller sheath and will increase the difficulty and risk of the surgery.

Technical Solution

The present invention solves the aforementioned technical problem by adopting the following technical scheme: an occluder comprising a distal end, a proximal end, and an elastic braided body provided between said distal end and proximal end and made of wires; said elastic braided body comprises a multistage braided mesh; said multistage braided mesh comprises at least a first-stage braided mesh, which is the closest to the distal end and is formed by braiding a plurality of first-stage wires, and a second-stage braided mesh, which is formed by braiding a plurality of first-stage wires and second-stage wires all together; the smallest cross-sectional area of the first-stage braided mesh after being compressed in the direction perpendicular to the axial direction of the elastic braided body is smaller than the smallest cross-sectional area of any other stage of braided mesh after being compressed toward the axis.

In the occluder of the present invention, all of the wires at said proximal end are tightened up and fixed through a bolt head so that the proximal end is closed.

In the occluder of the present invention, each stage of braided mesh is provided with an edge that is close to said distal end, and an opening is formed on the edge of said first-stage braided mesh.

In the occluder of the present invention, all of said edges are formed by the bent parts of said wires.

In the occluder of the present invention, each wire of the edge of any stage of braided mesh is bent into a thin ring that can deform along with twisting of said wire.

In the occluder of the present invention, a flexible ring with a corresponding fixed circumference is provided on the edge of any stage of braided mesh. Said flexible ring penetrates said bent part to prevent the corresponding wires from scattering. Said opening is reduced or closed when the circumference of the flexible ring provided on the edge of said first-stage braided mesh is reduced.

In the occluder of the present invention, said flexible ring is formed by penetrating one of the wires through said bent parts of the same stage of wires, and said flexible ring surrounds the perimeter of said edge.

In the occluder of the present invention, a small ring is provided in the bent part of each wire of the same stage, and said flexible ring penetrates the said small rings of the wires of the same stage to prevent the corresponding wires from scattering.

In the occluder of the present invention, the first-stage wires are made of a shape memory alloy material or a stainless steel material or a bioabsorbable material, and the second-stage wires are made of a shape memory alloy material or a stainless steel material.

In the occluder of the present invention, a closure head made of a bioabsorbable material is provided at the center of the first-stage braided mesh located at the distal end of the occluder.

In the occluder of the present invention, said bioabsorbable material includes magnesium or magnesium alloy material.

In the occluder of the present invention, said occluder also comprises a flow-occluding membrane and a suture thread provided in said multistage braided mesh, and said suture thread fixes said flow-occluding membrane on said multistage braided mesh.

The occluder of the present invention also comprises a connector provided at the proximal end.

The present invention also provides an occluder manufacturing method comprising the following steps:

Step 1: a plurality of wire hanging bars are provided at one end of a molded rod; the wire hanging bars are distributed on a plurality of concentric circles outwards from the axis of the molded rod; the wire hanging bars of the same stage are located on the same circle; a wire is wound on each wire hanging bar, and two branches of each wire are led out thereof;

Step 2: the branches of the wires are used to form a tubular multistage braided mesh on the molded rod; the wires on the wire hanging bars of the first stage on the innermost side are first braided into the first-stage braided mesh; then, the wines on the wire hanging bars of the first stage on the innermost side and the wires on the wire hanging bars of the second stage that is on the slightly outer side are braided into the second-stage braided mesh, followed by sequentially braiding the wires of the other stages; after that, all of the wires are braided along the sidewall of the molded rod into a long tubular shape until the desired mesh tube length is reached;

Step 3: a heat treatment is performed on the braided mesh on the molded rod to fix it into a stable mesh structure; the opening formed at the center of the first-stage braided mesh of said braided mesh is smaller than the diameter of the mesh tube, and said opening is located at the distal end of said occluder;

Step 4: the other end of the braided mesh is tightened up and fixed to form the proximal end of said occluder; a closed cavity is formed between the distal end and the proximal end of said occluder;

Step 5: the braided mesh is set in a heat setting mold to provide it with the shape and sufficient elasticity required for the occluder.

In the manufacturing method of the present invention, a connector for the occluder is fixed at the proximal end of the occluder in said step 4.

The manufacturing method of the present invention further comprises a step, in which the flow-occluding membrane is sewed in the cavity formed by the braided mesh after the occluder is shaped.

The manufacturing method of the present invention further comprises a step in which a flexible wire sequentially penetrates the first-stage wires on the edge of the opening of the first-stage braided mesh, followed by connecting the flexible wire into a flexible ring so that the scatter range of the first-stage wires on the edge of the first-stage braided mesh is limited by the circumference of the flexible ring.

Beneficial Effects

Compared with the prior art, the present invention has the following merits. Since the occluder of the present invention has no permanent metal closure head, the amount of the metal released by the occluder over the long term is reduced. The long-term electrochemical corrosion in that part is eliminated. The long-term damage caused by the permanent protrusion of the closure head to the tissues of the human body can be avoided. The occluder of the present invention is more conducive to epithelialization by the host tissue. In addition, since the occluder of the present invention has a multistage braided mesh, wire accumulation incurred when the distal end of the occluder is placed back into the sheath can be well avoided. The resistance of entering the sheath can be reduced significantly so that the occluder is suitable for smaller sheaths to lower the difficulty and risk of the surgery. The occluder of the present invention is more suitable for younger patients with relatively small blood vessels.

BRIEF DESCRIPTION OF THE DRAWINGS

In the following, the present invention will be explained in more detail with reference to the attached figures and embodiments.

FIG. 1 is a front view of an existing occluder equipped with a closure head.

FIG. 2 is a right-side view of the occluder shown in FIG. 1 equipped with a closure head.

FIG. 3 is a front view of an existing occluder having no closure head.

FIG. 4 is a right-side view of the occluder shown in FIG. 3 having no closure head but having wire accumulation in the middle.

DETAILED DESCRIPTION

Figure 5:
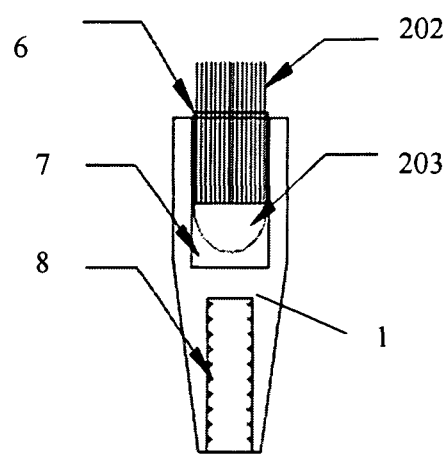
FIG. 5 is a structural diagram of a bolt head normally used for occluder connector.

In order to further clarify the objective, technical scheme, and merits of the present invention, in the following, the present invention will be explained in more detail with reference to the attached figures and embodiments. The present invention, however, is not limited to the embodiments to be described below.

The present invention provides an occluder comprising a distal end (defined as the end away from the operator during the operation), a proximal end (defined as the end close to the operator during the operation), and an elastic braided body provided between said distal end and proximal end. The elastic braided body has a cylindrical shape with variable diameter and including a plurality of grids. It comprises at least a first-stage braided mesh formed by braiding a plurality of first-stage wires and a second-stage braided mesh formed by braiding a plurality of first-stage wires and second-stage wires all together. Two stages of braided meshes are used in this embodiment of the present invention. However, it is also possible to adopt a third-stage braided mesh. The third-stage braided mesh is formed by jointly braiding the first-stage wires, the second-stage wires, and the third-stage wires, and so on. The number of the wires in the first-stage braided mesh is less than the number of wires in any other stage. In the expanded state, the grids of the first-stage braided mesh are sparser than the grids of the braided mesh of any other stage. The minimum cross-sectional area of the first-stage braided mesh after being compressed toward the axis is smaller than that of the braided mesh of any other stage after being compressed toward the axis. The braided mesh can be compressed into a sheath. When the external force is removed it can automatically resume the preset expanded state.

An opening can be formed at the distal end of the occluder. This opening is located at the center of the first-stage braided mesh and is formed through the edge of the first-stage braided mesh. The braided mesh at the proximal end of the occluder is tightened up and fixed through a bolt head so that the proximal end is closed. It is preferred to form the braided mesh by braiding a shape memory alloy, such as nickel-titanium alloy wires. The occluder can be provided with super elasticity through a heat treatment. The braided mesh can also use stainless steel or other metal material or other elastic materials suitable for the human body. Using nickel-titanium alloy wires can guarantee that the occluder automatically resumes the original shape after being released from a sheath having a smaller diameter than the occluder to occlude cardiac septal defects or blood vessels, and maintains sufficient radial support force to prevent the occluder from having displacement. The first-stage braided mesh can also use a bioabsorbable metal material, or an absorbable closure head can be added. This closure head can close up and fix the first-stage braided mesh at the distal end. The first-stage braided mesh and the closure head that can be absorbed by the human body can be made of pure magnesium or medical magnesium alloy.

The first-stage braided mesh starts from the distal end of the occluder and ends on the circumferential edge of the second-stage braided mesh. There is continuous transition between the first-stage braided mesh and the second-stage braided mesh. The braided mesh of each stage ends on the circumferential edge of the braided mesh of the next stage, and there is continuous transition between the two adjacent braided meshes. The multistage braided mesh constitutes a continuous braided body. The braided mesh of the final stage ends at the proximal end of the occluder. Therefore, the edge of the first-stage braided mesh is closer to the distal end of the occlude than the edge of the braided mesh of any other stage. The edge of the braided mesh of each stage is formed by bending and interlocking the continuous wires. Preferably, each wire on the edge is bent into a small ring, which can deform along with the twisting of that wire.

Furthermore, a flexible ring with a fixed circumference is provided on the edge of the braided mesh of each stage. The flexible ring penetrates the bent parts of the wires on the edge of the braided mesh of each stage to prevent the wires on the edge of the braided mesh of each stage from scattering. This flexible ring is formed by winding one wire around the edge of the braided mesh of each stage by one circle. This wire penetrates the bent parts of the other wires on the edge of the braided mesh of each stage and is then braided in the same way as the other wires. In particular, a flexible ring is provided on the edge of the first-stage braided mesh. As the circumference of this flexible ring is reduced, the opening can be shrunk or almost closed.

The flexible ring provided on the edge of the braided mesh of each stage can also be formed using suture thread. The opening at the center of the braided mesh of the present invention can also be sutured to increase the stability of the braided mesh. The diameter of the opening left after the opening is sutured can be selected based on the sizes of different occluders and the requirement on the support force. It is possible to maintain the original aperture or reduce the aperture or even tighten up and close the opening.

The occluder of the present invention can also include a flow-occluding membrane and suture threads. The flow-occluding membrane is fixed on the braided mesh by the suture threads. A connector can also be provided at the proximal end.

The occluder having the multistage braided mesh can be used as various kinds of cardiac occluders, such as ventricular septal defect (VSD) occluder, atrial septal defect (ASD) occluder, patent ductus arteriosus (PDA) occluder, patent foramen ovale (PFO) occluder, or vascular occlusion device. It can also be used in other medical fields that require occlusion or used for repairing local blood vessels.

The present also provides a method for manufacturing occluder having multistage braided mesh that comprises the following steps:

Step 1: a plurality of wire hanging bars are provided at one end of a molded rod; the wire hanging bars are distributed on a plurality of concentric circles outwards from the axis of the molded rod; the wire hanging bars of the same stage are located on the same circle; a wire is wound on each wire hanging bar, and two branches of each wire are led out;

Step 2: the branches of the wires are used to form a tubular multistage braided mesh on the molded rod; the wires on the wire hanging bars of the first stage on the innermost side are first braided into the first-stage braided mesh; then, the wires on the wire hanging bars of the first stage on the innermost side and the wires on the wire hanging bars of the second stage that is on the slightly outer side are braided into the second-stage braided mesh, followed by sequentially braiding the wires of the other stages; after that, all of the wires are braided along the sidewall of the molded rod into a long tubular shape until the desired mesh tube length is reached;

Step 3: a heat treatment is performed on the braided mesh on the molded rod to fix it into a stable mesh structure; the opening formed at the center of the first-stage braided mesh of said braided mesh is smaller than the diameter of the mesh tube, and said opening is located at the distal end of said occluder;

Step 4: the other end of the braided mesh is tightened up and fixed to form the proximal end of said occluder; a closed cavity is formed between the distal end and the proximal end of said occluder;

Step 5: the braided mesh is set in a heat setting mold to provide it with the shape and sufficient elasticity required for the occluder.

The occluder manufacturing method of the present invention can also comprise one or both of the following steps: a flow-occluding membrane is sutured in the braided mesh to the shaped occluder to improve the blood occluding effect; also, a flexible wire sequentially penetrates the first-stage wires on the edge of the opening of the first-stage braided mesh, followed by connecting the flexible wire into a flexible ring so that the scatter range of the first-stage wires on the edge of the first-stage braided mesh is limited by the circumference of the flexible ring to increase the stability of the structure of the braided mesh.

In the following, the braiding process and the tools used for the occluder of the present invention will be explained based on a plurality of embodiments.

Embodiment 1

Figure 6:
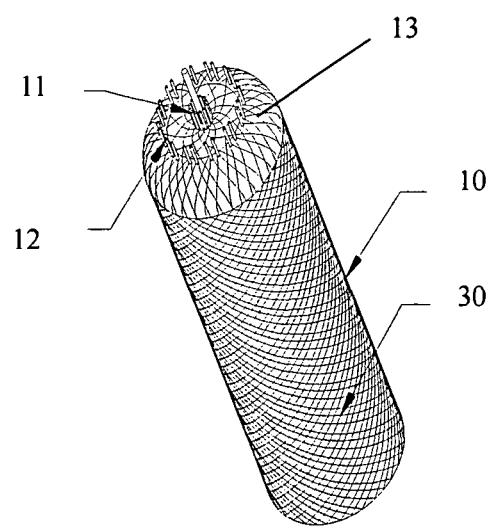
FIG. 6 is a diagram illustrating a metal mesh tube braided in stages on a molded rod.

As shown in FIG. 6, nickel-titanium alloy wires are first used to braid a metal mesh tube 30 on a cylindrical metal molded rod 10. A braiding chuck 13 is provided in the head part of molded rod 10. Holes are formed on two concentric circles around the axis of molded rod 10. Twelve holes are arranged symmetrically with respect to the axis on the first circle. Twenty-four holes are arranged on the outer second circle. Twelve rays are led out from the center of the circle to the twelve holes on the inner circle and cross with the outer circle at twelve points. These twelve points and the twenty-four holes on the outer circle are uniformly distributed on the outer circle. There are two holes between two adjacent points. A two-stage braided mesh is formed in this embodiment. Therefore, it is necessary to form two circles of holes on braiding chuck 13. Similarly, a plurality of circles of holes can be formed for a multistage braided mesh, and the braiding method is also similar.

Figure 7:
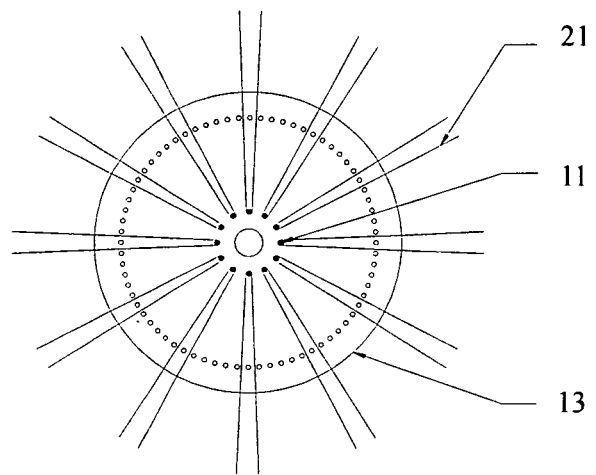
FIG. 7 is a top view illustrating the state when the wires of the first stage are hung on the first-stage wire hanging bars.
Figure 8:
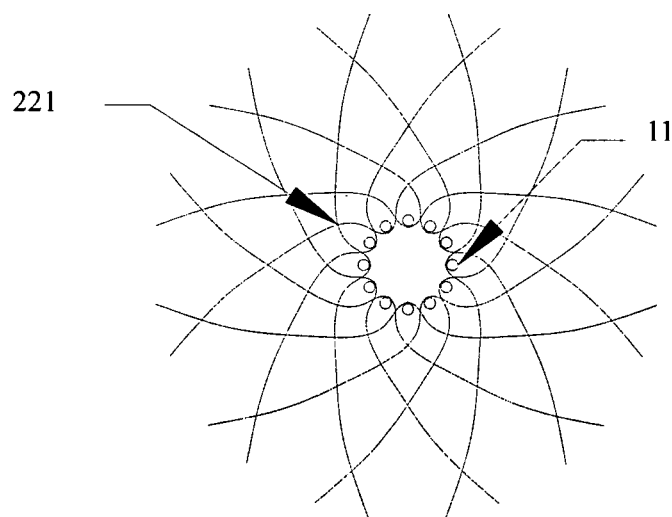
FIG. 8 is a diagram illustrating the first-stage braided mesh.
Figure 9:
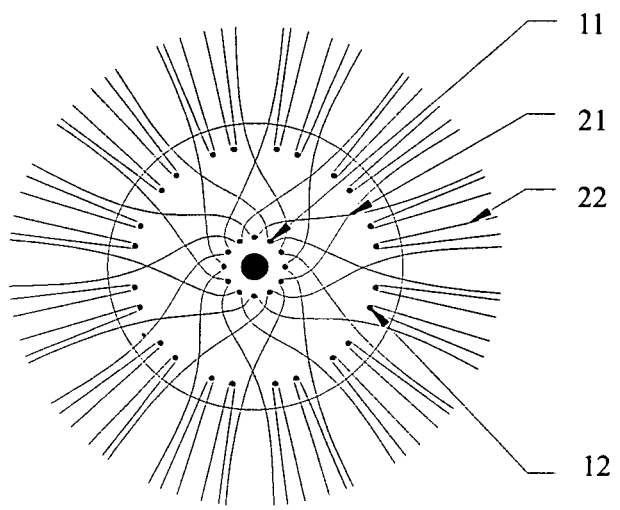
FIG. 9 is a top view illustrating the state when the wires of the second stage are hung on the second-stage wire hanging bars.
Figure 10:
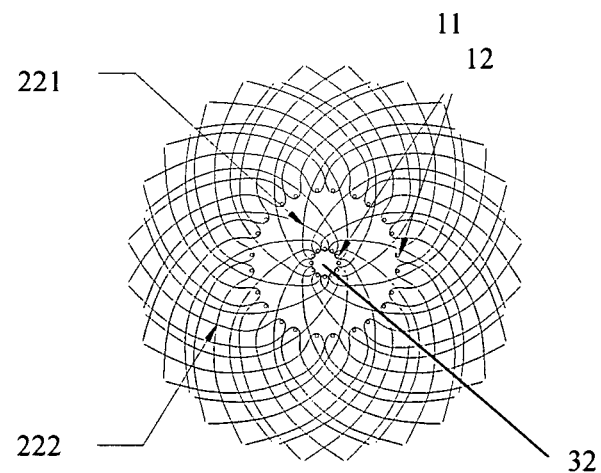
FIG. 10 is a diagram illustrating the state when the second-stage braided mesh is braided on the basis of the first-stage braided mesh.

To manufacture the first-stage braided mesh 221 shown in FIG. 8, the first-stage wire hanging bars 11 are inserted into the respective holes on the first circle, followed by hanging the first-stage wire 21 on each first-stage wire hanging bar 11. FIG. 7 shows the state viewed from right above the braiding chuck at that time. Each first-stage wire 1 is wound around the corresponding first-stage wire hanging bar 11 and is bent to the same angle to form two branches. All of the branches of the first-stage wires 21 are pulled tightly to successively cross with the adjacent first-stage wires 21. A net is formed as shown in FIG. 8 after three rounds of braiding. After the first-stage braided mesh 221 is braided, the second-stage wire hanging bars 12 are inserted into the holes on the outer circle, followed by hanging the second-stage wires 22 on the respective second-stage wire hanging bars 12 and mixed braiding them with the first-stage wires 21. FIG. 9 shows the braiding process viewed from right above the braiding chuck. FIG. 10 shows the effect after the braiding. The first-stage braided mesh 221 includes twelve first-stage wires 21 and has a total of twenty-four branches. The second-stage braided mesh 222 includes twelve first-stage wires 21 and the newly added twenty-four second-stage wires 22 and has a total of seventy-two branches. Therefore, the first-stage braided mesh 221 has different grid density from the second-stage braided mesh 222. The first-stage braided mesh 221 is sparser than the second-stage braided mesh 222. The first-stage braided mesh 221 has higher space compression ratio. There is a round opening 32 at the center of the first-stage braided mesh 221. It is used as the opening at the distal end of the occluder. In this embodiment, the first-stage braided mesh 21 and the second-stage braided mesh 22 are made of nickel-titanium alloy wires.

Figure 11:
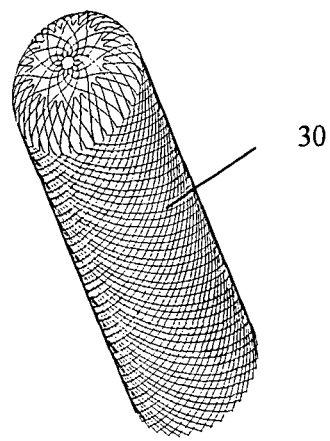
FIG. 11 shows the metal mesh tube with a stable structure when it is removed from the molded rod after heat setting.
Figure 12:
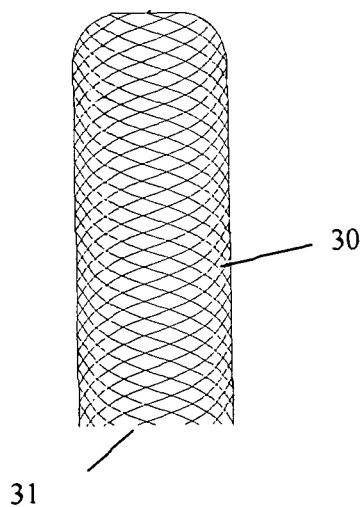
FIG. 12 is a side view of an opening at the distal end of the metal mesh tube.

During the braiding process, the wires first wrap around braiding chuck 13 and then covers the side surface of molded rod 10 to form a tubular shape. When a certain braiding length is completed, the tubular multistage braided mesh is fixed on molded rod 10, and a heat treatment is carried out to form a stable tubular structure. FIG. 11 shows metal mesh tube 30 removed from molded rod 10. FIG. 12 is the side view of FIG. 11. The bent parts of the first-stage wires 21 (the parts surrounding the first-stage wire hanging bars 11) constitute the boundary of the round opening of the first-stage braided mesh 221. The bent parts of the second-stage wires 22 (the parts surrounding the second-stage wire hanging bars 12) constitute the boundary of the second-stage braided mesh 222. The diameter of the boundary of the second-stage braided mesh 222 is bigger than the diameter of the opening of the first-stage braided mesh 221. The free ends of both the first-stage wires, 21 and the second-stage wires 22 end at the cylindrical opening 31 in the tail part of the metal mesh tube (as shown in FIG. 12). The diameter of the cylindrical opening 31 in the tail part of metal mesh tube 30 is bigger than the diameter of the boundary of the second-stage braided mesh 22. The first-stage braided mesh 221 at the distal end of the occluder comprising the aforementioned multistage braided mesh is formed by braiding a relatively small number of wires. A smaller cross-sectional area can be realized after the distal end thereof is compressed toward the axial line so that the occluder can be easily included in a fine sheath.

Figure 13:
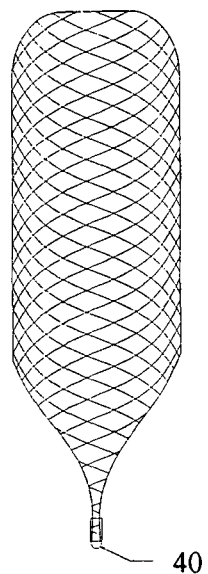
FIG. 13 is a side view illustrating the state when the wires at the proximal end of the metal mesh tube are tightened up and welded together with the steel sleeve.
Figure 14:
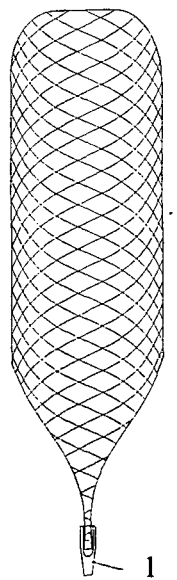
FIG. 14 is a side view of the welded bolt head at the proximal end of the metal end tube.

The tail part of metal mesh tube 30 is tightened up, and a steel sleeve 40 is used to fix the ends of all of the wires to close the proximal end of metal mesh tube 30, while the stage braided structure is kept at the other end. Then, the ends of the wires are welded together with steel sleeve 40 to form the proximal end of metal mesh tube 30, as shown in FIG. 13. After that, a connector is fixed at the proximal end. The bolt head structure shown in FIG. 5 can be used as this connector. A blind hole, wherein the steel sleeve can fit, is formed at one end of the connector, while an internally threaded hole is formed at the other end. The bolt head is set in the welding part and is fixed by means of welding as shown in FIG. 14.

Figure 15:
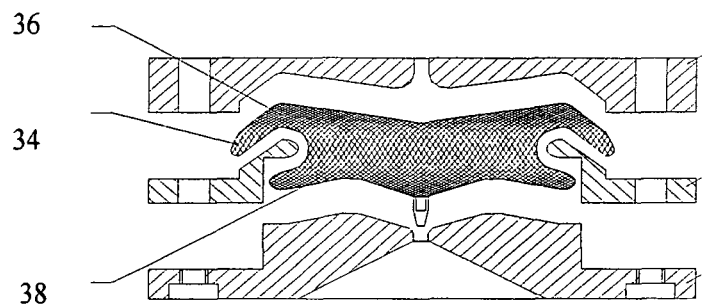
FIG. 15 is a cross-sectional view illustrating the state when the metal mesh tube is subjected to a heat treatment carried out in the mold to be shaped into a double-disc structure.
Figure 16:
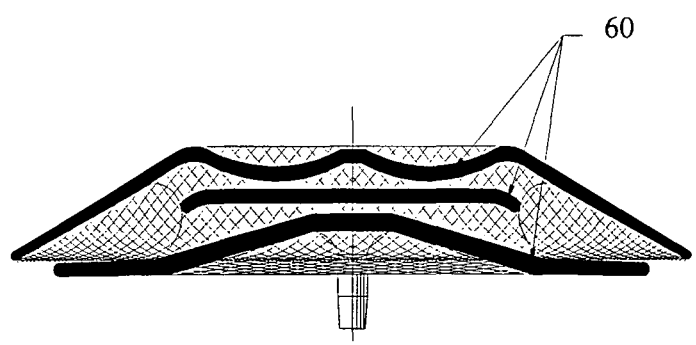
FIG. 16 is a side view illustrating the state when a flow-occluding membrane is sutured in the double-disc structure of the occluder.
Figure 17:
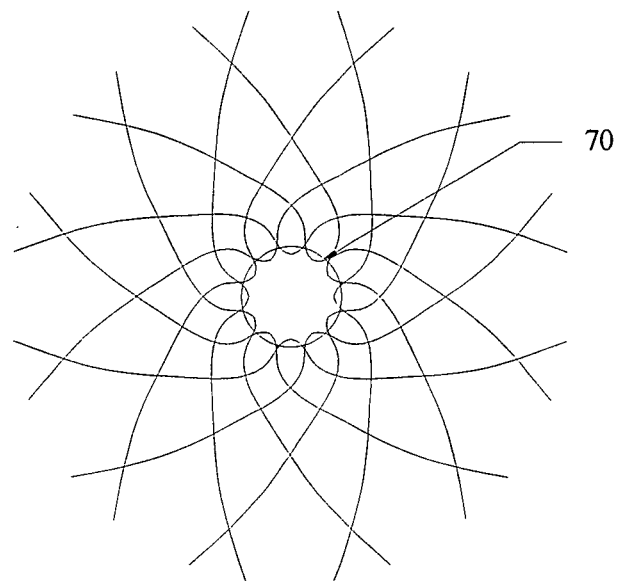
FIG. 17 is a diagram illustrating the state when the suture thread penetrates the first-stage wires on the edge of the first-stage braided mesh and is connected to form a ring.
Figures 18, 19:
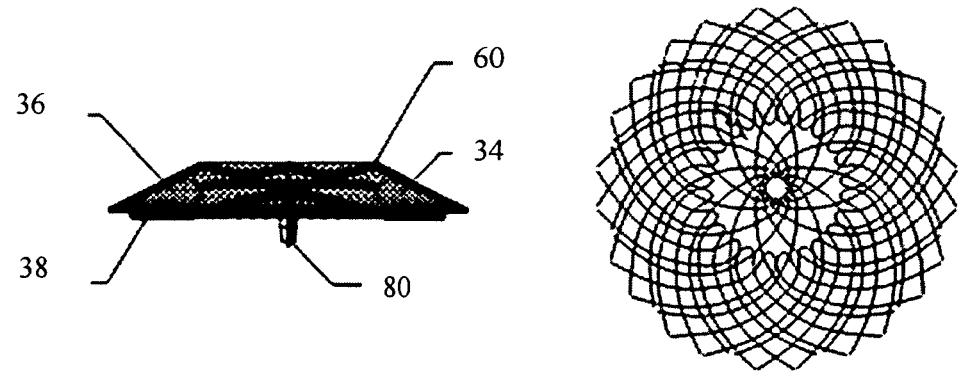
FIG. 18 is a front view of the occluder including a multistage braided mesh, wherein an opening is formed at the center of the first-stage braided mesh.
FIG. 19 is a top view of the occluder shown in FIG. 18.

Then, metal mesh tube 30 is set in a set of molds (including upper mold, middle mold, and lower mold), wherein a heat treatment is carried out for heat setting as shown in FIG. 15. The original metal mesh tube is extruded into a double-disc shaped braided body 34. The part of the multistage braided mesh close to the distal end is set in the upper mold to form the first disc surface 36. The bolt head and the other part of metal mesh tube 30 close to the proximal end are set in the upper mold to form the second disc surface 38. The middle mold is used to define the waist part between the two disc surfaces. The entire occluder has a symmetric structure with respect to the axis. Based on the actual demand, it can also be formed into other shapes, such as columnar shape or disc shape. Then, round flow-occluding membrane 60 comprising a polyester membrane or a polytetrafluoroethylene membrane is sutured using suture thread 70 at three positions, that is, the position with the biggest diameter of the first disc surface 36, the position with the biggest diameter of the second disc surface 38, and the waist part between the two discs in braided body 34 (see FIG. 17) as shown in FIG. 16. For the shaped occluder, suture thread 70 is used to successively penetrate the bent parts of the first-stage wires 21 to form a flexible ring with a certain circumference so that the structure of the multistage braided mesh becomes more stable as shown in FIG. 17. The finished product of the occluder is shown in FIGS. 18 and 19. The entire occluder includes braided body 34, the flow-occluding membrane 60 provided inside braid body 34, and bolt head 80 on one side of braided body 34. Braided body 34 includes the multistage braided mesh, which is divided into the first disc surface 36 and the second disc surface 38. There is a round opening 32 at the distal end. The multistage braided mesh includes the first-stage braided mesh 221 and the second-stage braided mesh 222.

Embodiment 2

Figure 20:
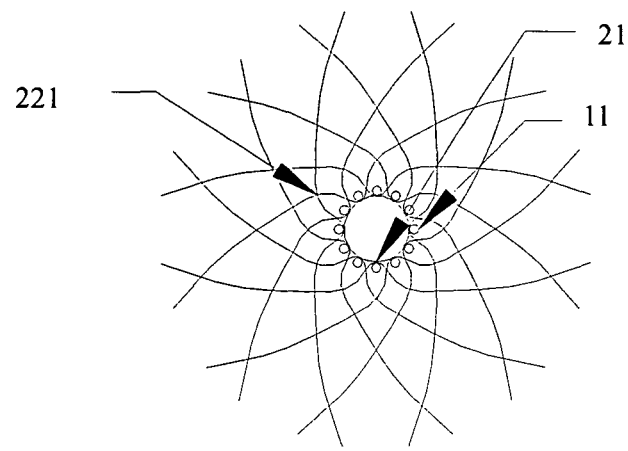
FIG. 20 is a diagram illustrating the state when one of the first-stage wires is formed into a ring after penetrating the other wires, followed by being hung on the corresponding first-stage wire hanging bar.

The second embodiment of the present invention is modified based on the first embodiment. When placing the first-stage wires 21, one of the first-stage wires penetrates the bent parts of all the other first-stage wires on the first-stage wire hanging bars 11. This first-stage wire is hung on the corresponding first-stage wire hanging bar 11 after it forms a ring around the other first-stage wire hanging bars 11 on the same circle, followed by starting braiding of the first-stage braided mesh 221, as shown in FIG. 20. The steps thereafter are basically the same as those of the first embodiment except that the step of using suture thread 70 to connect opening 32 is omitted, because the same objective can be achieved by the second embodiment.

Embodiment 3

Figure 21:
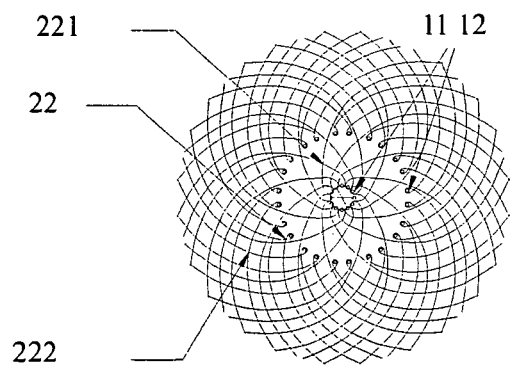
FIG. 21 is a diagram illustrating the state when each second-stage wire is formed into a ring around the corresponding second-stage wire hanging bar, followed by being divided into two branches for braiding.

The third embodiment is modified based on the first embodiment of the present invention. The first several steps are exactly the same as those of the first embodiment. When placing the second-stage wires 22, each second-stage wire 22 forms a small ring around one second-stage wire hanging bar 12, followed by braiding the two formed branches of each wire as shown in FIG. 21. The steps thereafter are exactly the same as those of the first embodiment. When the wires are bent into small rings, they are difficult to break during compressive deformation so that the safety of the metal mesh can be improved. The suture thread can also easily penetrate these small rings.

Embodiment 4

Figure 22:
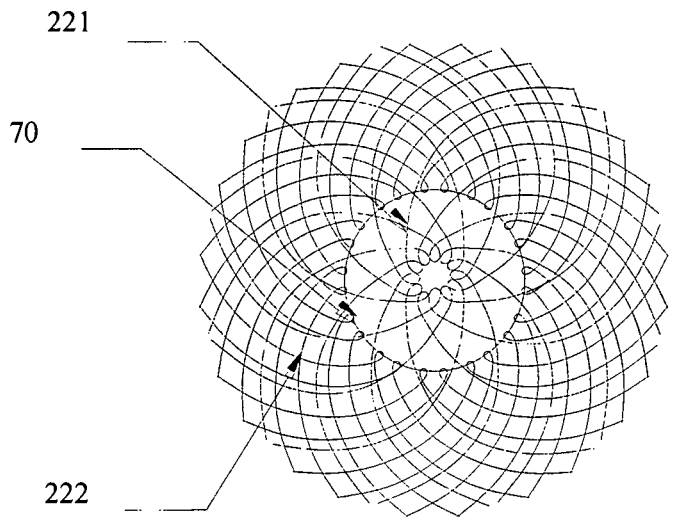
FIG. 22 is a diagram illustrating the state when a suture thread is used to penetrate all the small rings on the edge of the second-stage wires to connect them together.

The fourth embodiment of the present invention is modified based on the third embodiment. The manufacturing steps and method are basically the same as those of the third embodiment. The only difference is that after the occluder is shaped, suture thread 70 is used to penetrate the small rings formed by bending the second-stage wires 22 so that the boundary of the second-stage braided mesh 222 is restrained by the circumference of the closed suture thread 70 to further stabilize the structure of the occluder, as shown in FIG. 22.

Embodiment 5

Figure 23:
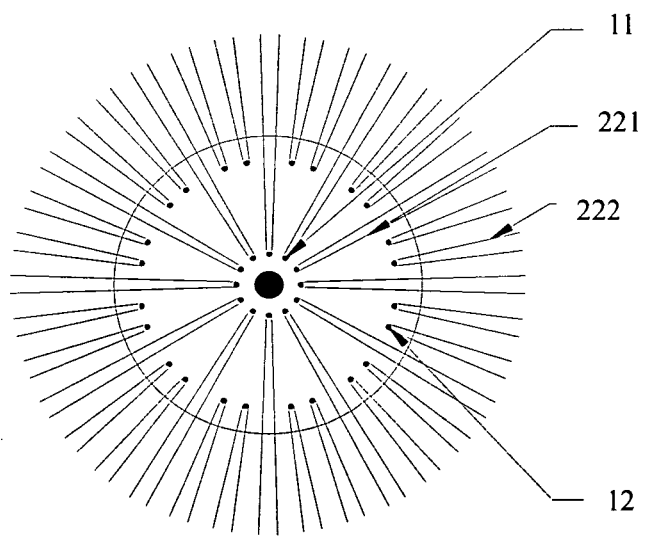
FIG. 23 is a diagram illustrating the state when the second-stage wires are hung after the first-stage wires are hung and the wires of the two stages do not cross with each other.
Figure 24:
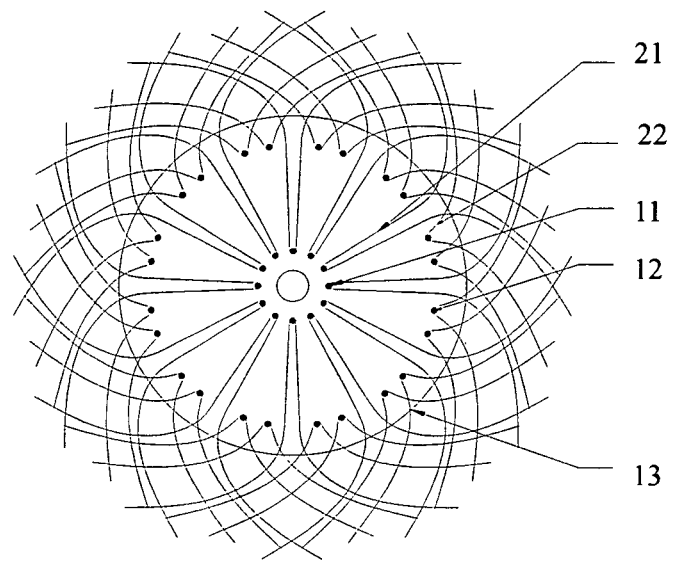
FIG. 24 is a top diagram illustrating the state when the first-stage wires and the second-stage wires are braided at the same time.
Figure 25:
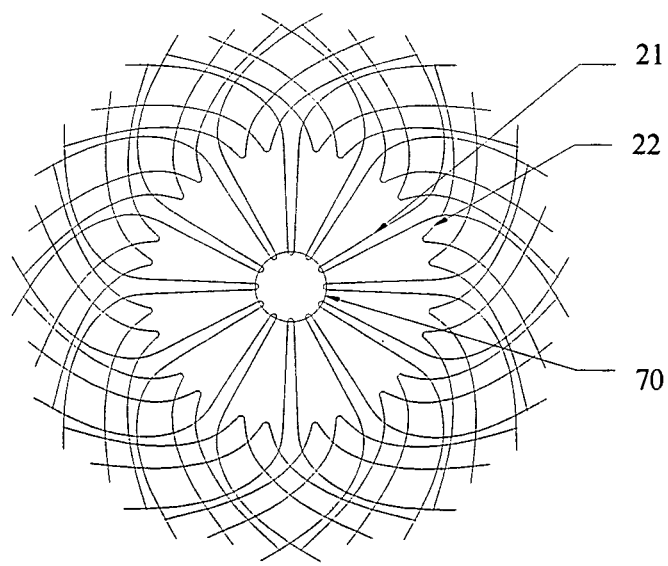
FIG. 25 is a diagram illustrating the state when a suture thread is used to connect the heads of the first-stage wires.

The fifth embodiment of the present invention is modified based on the first embodiment. The main difference between the fifth embodiment and the first embodiment is as follows. In this embodiment, the first-stage wires 21 are hung on the first-stage wire hanging bars 11. Instead of making the first-stage braided mesh, the second-stage wires 22 are hung on the second-stage wire hanging bars 12. FIG. 23 shows the state at that time from right above the braiding chuck. After the wires of the two stages are hung, seventy-two branches that are not forked are formed. Then, braiding is performed like the normal 72-wire mesh tube to obtain a multistage braided mesh. The effect is shown in FIG. 24. In order to stabilize the structure of the multistage braided mesh, finally, suture thread 70 is used to connect the head parts of the first-stage wires 21 to form the boundary of the opening 32 of first-stage braided mesh as shown in FIG. 25. This type of first-stage braided mesh is the sparsest and has the smallest cross-sectional area when compressed in the axial direction.

Embodiment 6

Figure 26:
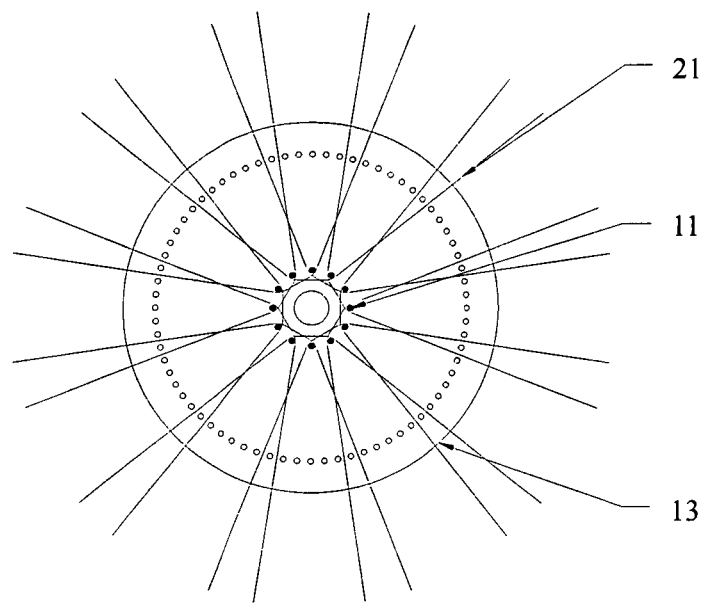
FIG. 26 is a top view illustrating the state when each first-stage wire crosses three first-stage wire hanging bars to form an alternate structure.
Figure 27:
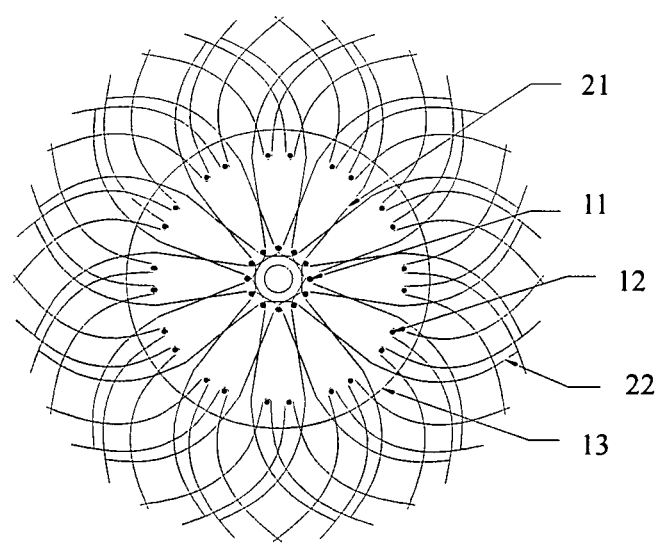
FIG. 27 is a top view illustrating the state when the second-stage wires are braided at the same time as the first-stage wires intertwined with the second-stage wires.
Figure 28:
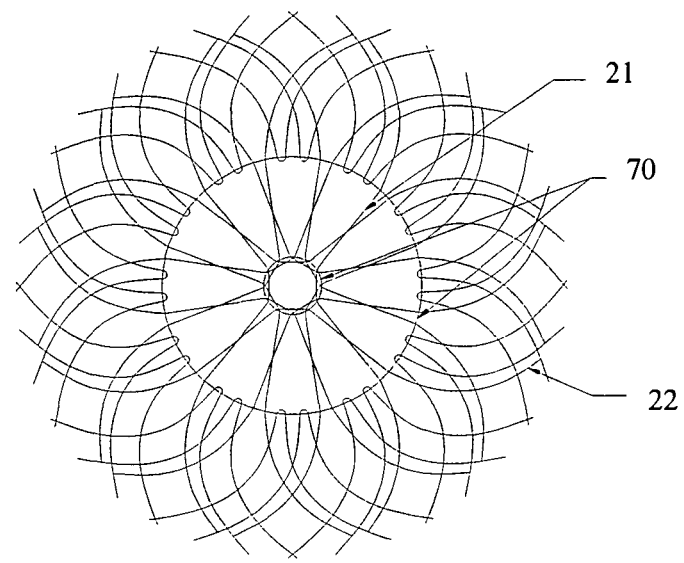
FIG. 28 is a diagram illustrating the state when two suture threads are used to connect the edges of the first-stage wires and the edges of the second-stage wires, respectively.

The sixth embodiment is modified based on the fifth embodiment. The main difference between the sixth embodiment and the fifth embodiment is as follows. In the sixth embodiment, each first-stage wire 21 crosses three first-stage wire hanging bars 11. One branch of each first-stage wire 21 crosses with one branch of another first-stage wire 21. These two wires are 90° rotationally symmetric to each other to form an alternate structure. FIG. 26 shows the state at that time when viewed from the above in the direction perpendicular to the braiding chuck. The second-stage wires 22 are hung right after hanging of the first-stage wires 21. The wires of these two stages form seventy-two branches. Each pair of crossed branches among the first-stage wires 21 become two adjacent sections. FIG. 27 shows the braiding process. In order to stabilize the structure, finally, suture thread 70 is used to restrain opening 32 and the boundary of the second-stage braided mesh 222 as shown in FIG. 28.

In any of the embodiments described above, a bioabsorbable material can be used for the first-stage braided mesh 21. A lot of research has shown that magnesium can be absorbed by the human body and has very good hemocompatibility. Therefore, said first-stage wires 21 can be replaced with pure magnesium wires or medical magnesium alloy wires. The occluder is formed by interweaving two kinds of wires: magnesium is used to form the first-stage braided mesh 221 to reduce the resistance incurred when the occluder is placed back into the sheath; the second stage braided mesh 222 is still made of nickel-titanium alloy to provide super elastic support structure. Under normal circumstances, after an occluder is implanted into the human body, the surface of the occluder will be quickly wrapped with the endothelial tissue. After two to four months, the magnesium mesh is gradually absorbed by the human body, while only the nickel-titanium alloy mesh with an integral structure is left. There will be no spikes left by a beheaded mesh. The defective part has also healed after the occluder is completely wrapped by the tissues of the human body. Even if the first-stage braided mesh 221 disappears, the second-stage braided mesh 222 will not loosen up. Since the magnesium is quickly eliminated from the body through metabolism, the occluder left in the human body has a relatively small amount of metal. Therefore, the long-term release of harmful metal is alleviated.

Figure 29:
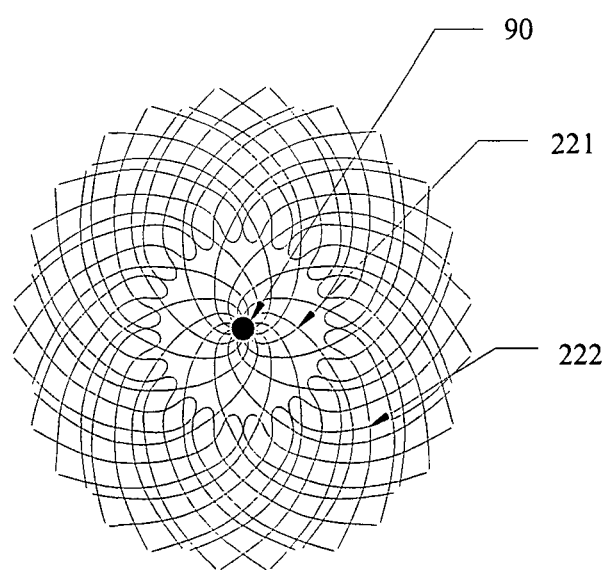
FIG. 29 is a diagram illustrating the first-stage braided mesh and the closure head made of a bioabsorbable material.

On the basis of the fifth embodiment, the first-stage wires 21 are replaced with pure magnesium wires or medical magnesium alloy wires. After the shape of the mesh tube is fixed, the heads of the first-stage wires 21 are gathered up and are fixed along with a closure head 90 made of magnesium as shown in FIG. 29. In this way, magnesium closure head 90 can further reduce the resistance when the occluder is placed back into the sheath. In the human body, magnesium closure head 90 and the first-stage wires 221 are gradually absorbed by the human body to reduce the amount of the remaining metal and the amount of the metal released over the long term. Since magnesium closure head 90 is absorbed by the human body, the long-term electrochemical corrosion between the closure head and the wires can be avoided. The magnesium closure head will not wear human tissue like the permanent closure head, either.

Only the preferred embodiments of the present invention have been described above. The present invention is not limited to these embodiments. Any modification, equivalent substitution or improvement made within the gist of the present invention should be included in the protection scope of the present invention.

What is claimed is:

1. An occluder comprising a distal end, a closed proximal end, and an elastic braided body provided between said distal end and proximal end and made of wires, wherein: said elastic braided body comprises a multistage braided mesh, said multistage braided mesh having at least a first-stage braided mesh, which is the closest to the distal end and is formed by braiding a plurality of first-stage wires, and a second-stage braided mesh, which is formed by braiding a plurality of the first-stage wires and second-stage wires together;
wherein the first-stage wires have bent parts that circumscribe a first opening at a terminal distal end of the first-stage braided mesh, and the second-stage wires have bent parts that circumscribe a second opening at a terminal distal end of the second-stage braided mesh, with the second opening having a diameter that is bigger than the diameter of the first opening and wherein the first opening is distal the second opening and radially inward to the second opening.

2. The occluder of claim 1, wherein at least the second stage wires at said proximal end are tightened up and fixed through a bolt head so that the proximal end is closed.

3. The occluder of claim 1, wherein the first opening is formed through a distal edge of the first-stage braided mesh and extends through the elastic braided body, wherein the occluder comprises a first flexible ring provided on the distal edge of the first-stage braided mesh and around the first opening, and a second flexible ring is provided on the second opening of the second-stage braided mesh.

4. The occluder of claim 3, wherein said first flexible ring penetrates at least one of said bent parts of the first-stage wires, and surrounds the distal edge of the first-stage braided mesh.

5. The occluder of claim 3, wherein each first-stage wire of the distal edge of the first-stage braided mesh is bent into a small ring.

6. The occluder of claim 5, wherein said first flexible ring penetrates at least one of said small rings.

7. The occluder of claim 1, wherein the first-stage wires are made of a bioabsorbable material, and the second-stage wires are made of a shape memory alloy material or a stainless steel material.

8. The occluder of claim 1, wherein each first-stage wire is bent to form branches that successively cross with adjacent first stage wires.

9. The occluder of claim 1, wherein the first stage wires are formed from magnesium, and the second-stage wires are made of nickel-titanium alloy.

10. The occluder of claim 1, wherein the first-stage braided mesh starts from the distal end of the occluder and ends on a circumferential edge of the second-stage braided mesh, with a continuous transition between the first-stage braided mesh and the second-stage braided mesh.

11. The occluder of claim 1, wherein the first-stage braided mesh has different grid density from the second-stage braided mesh.

* * * * *